United States Patent [19]
Midha et al.

[11] Patent Number: 6,165,457
[45] Date of Patent: *Dec. 26, 2000

[54] PERSONAL CARE COMPOSITIONS CONTAINING TOUGHENED GRAFTED POLYMERS

[75] Inventors: Sanjeev Midha, Blue Ash; Timothy Roy Nijakowski, Cincinnati, both of Ohio

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/854,513

[22] Filed: May 12, 1997

[51] Int. Cl.$^7$ ..................................................... A61K 31/74
[52] U.S. Cl. ..................................... 424/78.17; 424/78.18; 525/288; 525/301
[58] Field of Search .............................. 424/78.17, 78.18; 525/288, 301

[56] References Cited

U.S. PATENT DOCUMENTS

| | | | |
|---|---|---|---|
| 3,208,911 | 9/1965 | Oppliger | 167/87 |
| 3,862,077 | 1/1975 | Schulz | 260/29.6 |
| 3,957,970 | 5/1976 | Korkis | 424/70 |
| 3,965,021 | 6/1976 | Clemens | 525/72 |
| 4,030,512 | 6/1977 | Papantoniou et al. | 132/7 |
| 4,136,250 | 1/1979 | Mueller et al. | 528/29 |
| 4,185,087 | 1/1980 | Morlino | 424/70 |
| 4,277,595 | 7/1981 | Deichert et al. | 528/26 |
| 4,479,893 | 10/1984 | Hirota et al. | 252/542 |
| 4,563,347 | 1/1986 | Starch | 424/70 |
| 4,601,902 | 7/1986 | Fridd et al. | 424/70 |
| 4,636,578 | 1/1987 | Feinberg | 525/301 |
| 4,654,161 | 3/1987 | Kollmeier et al. | 252/174.15 |
| 4,659,777 | 4/1987 | Riffle et al. | 525/100 |
| 4,663,413 | 5/1987 | Ward et al. | 528/26 |
| 4,689,383 | 8/1987 | Riffle et al. | 528/12 |
| 4,693,935 | 9/1987 | Mazurek | 525/288 |
| 4,724,851 | 2/1988 | Cornwall et al. | 132/7 |
| 4,728,571 | 3/1988 | Clemens et al. | 428/352 |
| 4,733,677 | 3/1988 | Gee et al. | 132/7 |
| 4,743,643 | 5/1988 | Buter | 525/301 |
| 4,744,978 | 5/1988 | Homan et al. | 424/70 |
| 4,814,402 | 3/1989 | Nakashima et al. | 526/245 |
| 4,902,499 | 2/1990 | Bolich, Jr. et al. | 424/70 |
| 4,963,595 | 10/1990 | Ward et al. | 525/415 |
| 4,972,037 | 11/1990 | Garbe et al. | 526/245 |
| 4,981,902 | 1/1991 | Mitra et al. | 524/547 |
| 4,981,903 | 1/1991 | Garbe | 525/288 |
| 4,988,506 | 1/1991 | Mitra et al. | 424/81 |
| 5,021,477 | 6/1991 | Garbe et al. | 424/70 |
| 5,061,481 | 10/1991 | Suzuki et al. | 424/63 |
| 5,100,658 | 3/1992 | Bolich, Jr. et al. | 424/70 |
| 5,104,646 | 4/1992 | Bolich, Jr. et al. | 424/70 |
| 5,106,609 | 4/1992 | Bolich, Jr. et al. | 424/70 |
| 5,153,268 | 10/1992 | Legrow | 525/288 |
| 5,166,274 | 11/1992 | McGrath | 525/301 |
| 5,166,276 | 11/1992 | Hayama et al. | 525/329 |
| 5,219,560 | 6/1993 | Suzuki et al. | 424/63 |
| 5,229,022 | 7/1993 | Song | 525/301 |
| 5,229,435 | 7/1993 | Sakai et al. | 523/105 |
| 5,332,766 | 7/1994 | Takaya | 525/288 |
| 5,356,616 | 10/1994 | Sojka | 424/78.18 |
| 5,376,730 | 12/1994 | Niwano | 525/330.3 |
| 5,536,788 | 7/1996 | Deckers | 525/301 |
| 5,541,261 | 7/1996 | Fock | 525/301 |
| 5,578,683 | 11/1996 | Koch | 525/301 |
| 5,633,317 | 5/1997 | Kawasaki | 525/71 |
| 5,646,210 | 7/1997 | Timmerman | 525/288 |
| 5,665,823 | 9/1997 | Saxena | 525/288 |

FOREIGN PATENT DOCUMENTS

| | | | |
|---|---|---|---|
| 0 117 360 | 12/1983 | European Pat. Off. | A61K 7/06 |
| 0 408 311 A2 | 7/1990 | European Pat. Off. | C08F 230/08 |
| 56-092811 | 7/1981 | Japan | A61K 7/11 |
| 56-129300 | 10/1981 | Japan | A61K 7/06 |
| 4-359912 | 6/1991 | Japan | C08F 299/08 |
| 4-359913 | 6/1991 | Japan | C08F 299/08 |
| 4-360812 | 6/1991 | Japan | A61K 7/00 |
| WO 88/05060 | 7/1988 | WIPO | C08F 30/08 |
| 0 815 848 A1 | 1/1998 | WIPO | A61K 7/48 |

*Primary Examiner*—Paul R. Michl
*Attorney, Agent, or Firm*—Stephen T. Murphy; Andrew A Paul

[57] ABSTRACT

Disclosed are personal care compositions, such as haircare, cosmetic and nail compositions containing toughened grafted polymers.

18 Claims, No Drawings

PERSONAL CARE COMPOSITIONS CONTAINING TOUGHENED GRAFTED POLYMERS

TECHNICAL FIELD

The present invention relates to personal care compositions, such as haircare, cosmetic and nail compositions containing linear toughened grafted polymers.

BACKGROUND OF THE INVENTION

Cosmetic compositions such as lotions, creams, emulsions, packs, make-up (e.g., foundations, lipsticks, eye shadows and the like) and hair compositions are used to improve one's outward appearance. Many personal care products contain various resins, gums, and adhesive polymers. The polymers are used for a variety of purposes including thickening, feel properties, film-forming ability, active deposition, active penetration, hair holding, etc. Consequently there is constantly a search for developing polymers having improved properties for use in personal care product. For example, the desire to have the hair retain a particular shape is widely held. The most common methodology for accomplishing this is the application of a styling composition to dampened hair, after shampooing and/or conditioning, or to dry, styled hair. These compositions provide temporary setting benefits and they can be removed by water or by shampooing. The materials used in the compositions to provide the setting benefits have generally been resins and have been applied in the form of mousses, gels, lotions or sprays.

Many people desire a high level of style retention, or hold, from a hair spray composition. In typical hair sprays, hold is achieved by the use of resins, such as AMPHOMER®, supplied by National Starch and Chemical Company, and GANTREZ® SP 225, supplied by GAF. In general, as hair hold for hair spray compositions is increased, the tactile feel of the hair becomes stiffer and hence, less desirable. It is desirable to provide hair spray products which could provide an improved combination of hair hold and hair feel characteristics.

Recently, it has become known to utilize silicone grafted organic backbone polymers in various personal care compositions including their use as hair setting agents in hairspray compositions and other hair styling compositions, e.g. hair tonics, lotions, rinses, mousses, etc. Silicone grafted polymers can be used to make personal care compositions with improved feel, e.g., in the case of hair sprays, increased softness relative to conventional polymeric hair setting agents.

It remains desirable to improve the performance of grafted polymers. It is an object of this invention to provide personal care compositions containing toughened graft copolymers.

It is a further object of this invention to provide personal care compositions containing resins that have improved adhesive and cohesive properties and low creep at high humidity thereby providing improved style durability benefits.

These and other benefits as may be apparent from the description below can be obtained by the present invention.

The present compositions can comprise, consist of, or consist essentially of any of the required or optional ingredients and/or limitations described herein.

All percentages and ratios are calculated on a weight basis unless otherwise indicated. All percentages are calculated based upon the total composition unless otherwise indicated.

All ingredient levels refer to the active level of that ingredient, and are exclusive of solvents, by-products, or other impurities that may be present in commercially available sources, unless otherwise indicated.

SUMMARY OF THE INVENTION

The present invention relates to a personal care composition comprising:

(a) an adhesive copolymer, said copolymer being characterized by an organic polymeric backbone wherein said backbone has a Tg of from about 0° C. to about 45° C. wherein said copolymer comprises one or more side chains grafted thereon consisting of acrylic and methacrylic monomer units wherein each of said side chains has a Tg of greater than about 50° C.–200° C. wherein the number average molecular weight of said side chain is greater than about 1000; and (b) a personal care carrier.

DETAILED DESCRIPTION OF THE INVENTION

The essential components of the present invention are described below. Also included is a nonexclusive description of various optional and preferred components useful in embodiments of the present invention.

Grafted Adhesive Polymer

The compositions hereof will generally comprise from about 0.1% to about 99%, preferably from 0.5% to about 50%, more preferably from about 1% to about 10%, by weight of the composition, of the grafted polymer. It is not intended to exclude the use of higher or lower levels of the polymers, as long as an effective amount is used to provide adhesive or film-forming properties to the composition and the composition can be formulated and effectively applied for its intended purpose. By adhesive polymer what is meant is that when applied as a solution to a surface and dried, the polymer forms a film or a weld. Such a film will have adhesive and cohesive strength, as is understood by those skilled in the art.

The grafted polymers are characterized by acrylic and methacrylic monomer units covalently bonded to and pendant from a polymeric carbon-based backbone.

The backbone will preferably be a carbon chain derived from polymerization of ethylenically unsaturated monomers and wherein said backbone has a Tg of from about 0° C. to about 45° C.

The grafted polymer should have a weight average molecular weight of at least about 20,000. There is no upper limit for molecular weight except that which limits applicability of the invention for practical reasons, such as processing, aesthetic characteristics, formulateability, etc. In general, the weight average molecular weight will be less than about 10,000,000, more generally less than about 5,000,000, and typically less than about 3,000,000. Preferably, the weight average molecular weight will be between about 50,000 and about 2,000,000, more preferably between about 75,000 and about 1,000,000, most preferably between about 80,000 and about 750,000.

The term "graft copolymers" is familiar to one of ordinary skill in polymer science and is used herein to describe the copolymers which result by adding or "grafting" polymeric side chain moieties (i.e. "grafts") onto another polymeric moiety referred to as the "backbone". The backbone typically has a higher molecular weight than the grafts. Thus, graft copolymers can be described as polymers having pendant polymeric side chains, and as being formed from the "grafting" or incorporation of polymeric side chains onto or into a polymer backbone. The polymer backbone can be a homopolymer or a copolymer. The graft copolymers are derived from a variety of monomer units.

The graft polymers made in accordance with the methods herein can have a single Tg and preferably are copolymers having at least two distinct immicible phases, wherein the polymeric side chains are closely associated with each other and exist in one phase and polymeric backbone of the copolymer remains in a second separate phase. A consequence of this phase immiscibility is that if the temperature separation between each of the Tg's values involved is large enough then these copolymers exhibit two distinct Tg's, namely one Tg value for the backbone and one Tg value for the side chain. The term Tg means glass transition temperature, which is familiar to one of ordinary skill in the art. The copolymers can also exhibit a third glass transition temperature corresponding to any optional polysiloxane side chains on the graft copolymers. Whether such a third Tg value is observable depends upon a number of factors including the percent silicone in the copolymer, the number of polysiloxane side chains in the copolymer, the temperature separation between each of the Tg's values involved, and other such physical factors.

When used in a composition, such as a personal care composition for application to the hair or skin, the vehicle should permit the polymer to deposit on the intended surface, such as hair or skin.

Backbone Vinyl Monomer Units:

The copolymers of the present invention comprise from about 50% to about 98%, preferably from about 60% to about 95%, and more preferably from about 70% to about 90% by weight of the backbone vinyl monomer units.

The backbone vinyl monomer unit is selected from copolymerizable monomers, preferably ethylenically unsaturated monomers. The monomers are selected to meet the requirements of the copolymer. By "copolymerizable", as used herein, is meant that the vinyl monomer can be reacted with or polymerized with the acrylic or methacrylic macromonomers in a polymerization reaction using one or more conventional synthetic techniques, such as ionic, emulsion, dispersion, Ziegler-Natta, free radical, group transfer or step growth polymerization. In the present invention, monomers and macromonomers that are copolymerizable using conventional free radical initiated techniques are preferred. The term "ethylenically unsaturated" is used herein to mean a material that contains at least one polymerizable carbon-carbon double bond, which can be mono-, di-, tri- or tetra-substituted.

The monomer units can be derived from hydrophilic monomers (typically polar monomers), or mixtures of such hydrophilic monomers with hydrophobic monomers (typically low polarity monomers), provided that the solubility characteristics of the overall copolymer is achieved. As used herein, "hydrophilic monomers" means monomers which form homopolymers which are substantially water soluble; "hydrophobic monomers" means monomers which form substantially water insoluble homopolymers.

Preferred monomers include unsaturated alcohols, unsaturated monocarboxylic acids, unsaturated dicarboxylic acids, unsaturated anhydrides, alcohol esters of unsaturated monocarboxylic acids, alcohol esters of unsaturated dicarboxylic acids, alcohol esters of unsaturated anhydrides, alkoxylated esters of unsaturated monocarboxylic acids, alkoxylated esters of unsaturated dicarboxylic acids, alkoxylated esters of unsaturated anhydrides, aminoalkyl esters of unsaturated monocarboxylic acids, aminoalkyl esters of unsaturated dicarboxylic acids, aminoalkyl esters of unsaturated anhydrides, amides of unsaturated monocarboxylic acids, amides of unsaturated dicarboxylic acids, amides of unsaturated anhydrides, salts of unsaturated monocarboxylic acids, salts of unsaturated dicarboxylic acids, salts of unsaturated anhydrides, unsaturated hydrocarbons, unsaturated heterocycles, and mixtures thereof.

More preferred monomer units are selected from the group consisting of acrylic acid, methacrylic acid, N,N-dimethyl acrylamide, dimethylaminoethyl methacrylate, quaternized dimethylaminoethsyl methacrylate, vinyl pyrrolidone, $C_1$–$C_{18}$ alkyl esters of acrylic or methacrylic acid, styrene, alpha-methylstyrene, t-butylstyrene, vinyl acetate, vinyl propionate, vinyl chloride, vinylidene chloride, vinyl toluene, 2-methoxyethyl acrylate, n-butyl methacrylate, isobutyl methacrylate, t-butyl acrylate, t-butyl methacrylate, 2-ethylhexyl methacrylate, methyl methacrylate, salts of any acids and amines listed above, and combinations thereof.

Most preferred monomer units of said backbone selected from the group consisting of acrylic acid, methacrylic acid, 2-methoxyethyl acrylate, n-butyl methacrylate, isobutyl methacrylate, t-butyl acrylate, t-butyl methacrylate, 2-ethylhexyl methacrylate, methyl methacrylate and mixtures thereof.

The backbone has a Tg of from about 0° C. to about 45° C., preferably from about 0° C. to about 35° C., and most preferably from about 0° C. to about 25° C.

Acrylic and Methacrylic Macromonomer Side Chain Units

The copolymers of the present invention comprise from about 2% to about 50%, preferably from about 5% to about 40%, and more preferably from about 10% to about 30%, by weight of the copolymer of acrylic and methacrylic macromonomer side chain units.

The macromonomer units are copolymerizable with the vinyl monomers, said macromonomers preferably having a vinyl moiety. Either a single type of macromonomer unit or combinations or two or more macromonomer units can be utilized herein. The macromonomers are selected to meet the requirements of the copolymer. By "copolymerizable", as used herein, is meant that the macromonomers can be reacted with or polymerized with the vinyl monomers in a polymerization reaction using one or more conventional synthetic techniques, as described above.

The macromonomers that are useful herein contain a polymeric portion and a copolyermizable moiety which is preferably an ethylenically unsaturated moiety. Typically, the preferred macromonomers are those that are endcapped with the vinyl moiety. By "endcapped" as used herein is meant that the vinyl moiety is at or near a terminal position of the macromonomer.

The macromonomers can be synthesized utilizing a variety of standard synthetic procedures familiar to the polymer chemist of ordinary skill in the art. Furthermore, these macromonomers can be synthesized starting from commercially-available polymers. Typically, the weight average molecular weight of the macromonomer is from about 1000 to about 50,000.

Preferred macromonomers are poly(acrylate) and poly(methacrylate) macromonomers. Macromonomers are exemplified by the general formula:

wherein I is an optionally present initiator (i.e. n=0 or 1), W is a monomer unit, E is an endcapping group, and m is an integer from about 10 to about 2000.

I is an optionally present chemical initiator moiety. Without being limited by theory, I can be derived from a chemical initiator or solvent used in the synthesis of the macromonomer. Nonlimiting examples of such initiators from which I can be derived include hydrogen ion, hydrogen radical, hydride ion, hydroxide ion, hydroxyl radical, peroxide radical, peroxide anion, $C_1$–$C_{20}$ carbocations, $C_1$–$C_{20}$ carbanions, $C_1$–$C_{20}$ carbon radicals, $C_1$–$C_{20}$ aliphatic and aromatic alkoxy anions, ammonium ion, and substituted ammonium ions (e.g., $C_1$–$C_{20}$ alkyl and $C_1$–$C_{20}$ alkoxy substituted), and mixtures thereof. I can be derived from any useful solvent, nonlimiting examples of which include water, methanol, ethanol, propanol, isopropanol, acetone, hexane, dichloromethane, chloroform, benzene, toluene, and mixtures thereof.

W is selected from the group consisting of acrylic monomer units methacrylic monomer unit and mixtures thereof. Nonlimiting classes of such monomers acrylic acid $C_1$–$C_{18}$ straight and branched chain acrylate esters methacrylic acid and $C_1$–$C_{18}$ straight and branched chain methacrylate esters, and mixtures thereof.

Preferably the monomer units of the side chains are selected from the group consisting of acrylic acid (produced by hydrolysis of trimethylsilyl acrylate), methacrylic acid (produced by hydrolysis of trimethylsilyl methacrylate), phenyl methacrylate, benzyl methacrylate, and $C_1$–$C_{18}$ alkyl esters of acrylic or methacrylic acid and mixtures thereof. More preferably, the monomer units are selected from the group consisting acrylic acid (preferably produced by hydrolysis of trimethylsilyl acrylate), methacrylic acid (preferably produced by hydrolysis of trimethylsilyl methacrylic, n-propyl methacrylate, iso-butyl methacrylate, tert-butyl acrylate, tert-butyl methacrylate, 2-hydroxyethyl methacrylate (produced by hydrolysis of trimethylsilyl protected alcohol), 2-hydroxypropyl methacrylate (produced by hydrolysis of trimethylsilyl protected alcohol). Most preferred are monomer units of selected from the group consisting of acrylic acid (preferably produced by hydrolysis of trimethylsilyl acrylate), methacrylic acid (preferably produced by hydrolysis of trimethylsilylmethacrylate), n-propyl methacrylate, iso-butyl methacrylate and mixtures thereof.

Each side chain has a Tg of from about 50° C. to about 200° C., preferably of from about 60° C. to about 150° C. and most preferably of from about 70° C. to about 110° C.

Optionally, the adhesive copolymers can further comprise one or more polysiloxane macromonomer side chains exemplified by the general formula:

$$X(Y)_n Si(R)_{3-m} Z_m$$

wherein X is a vinyl group copolymerizable with the vinyl monomer units; Y is a divalent linking group; each R is independently selected from the group consisting of hydrogen, hydroxyl, $C_1$–$C_6$ alkyl, $C_1$–$C_6$ alkoxy, $C_2$–$C_6$ alkylamino, phenyl, $C_1$–$C_6$ alkyl or alkoxy-substituted phenyl; Z is a monovaient siloxane polymeric moiety having a number average molecular weight of at least about 1000, is essentially unreactive under copolymerization conditions; n is 0 or 1; and m is an integer from 1 to 3. The polysiloxane macromonomer Preferably, the polysiloxane macromonomer has a formula selected from the following formulas:

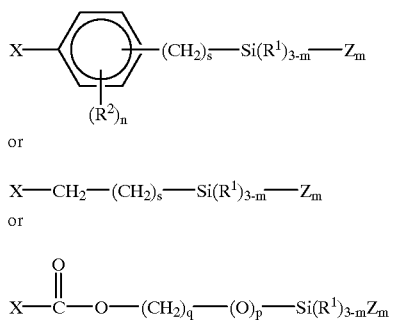

In these structures s is an integer from 0 to 6; preferably 0, 1, or 2; more preferably 0 or 1; m is an integer from 1 to 3, preferably 1; p is 0 or 1; q is an integer from 2 to 6; each $R^1$ is independently selected form the group consisting of hydrogen, hydroxyl, C1–C6 alkyl, C1–C6 alkoxy, C2–C6 alkylamino, phenyl, C1–C6 alkyl or alkoxy-substituted phenyl, preferably C1–C6 alkyl, or C1–C6 alkyl or alkoxy-substituted phenyl, more preferably C1–C6 alkyl, even more preferably methyl, $R^2$ is selected from the group consisting of C1–C6 alkyl or C1–C6 alkyl substituted phenyl, preferably methyl.

n is an integer from 0 to 4, preferably 0 or 1, more preferably 0; X is

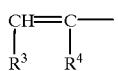

wherein $R^3$ is hydrogen or —COOH, preferably $R^3$ is hydrogen; $R^4$ is hydrogen, methyl or —CH$_2$COOH, preferably $R^4$ is methyl; Z is

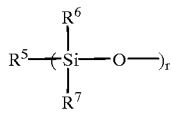

wherein $R^5$, $R^6$, and $R^7$, are independently selected from hydrogen, hydroxyl, C1–C6 alkyl, C1–C6 alkoxy, C2–C6 alkylamino, phenyl, C1–C6 alkyl or alkoxy-substituted phenyl, hydrogen or hydroxyl, preferably $R^5$, $R^6$, and $R^7$ are C1–C6 alkyls; more preferably methyl; and r is an integer of from about 14 to about 700, preferably about 60 to about 400, and more preferably about 100 to about 350.

Exemplary grafted polymers for use in the present invention include the following, where the composition is given as weight part of monomer used in the synthesis:

(i) poly(t-butyl acrylate-co-2-methoxyethyl acrylate-co-methacrylic acid)-graft-poly (n-propyl methacrylate-co-methacrylic acid) MWt of copolymer: 149,900 Backbone: 80% Backbone Composition: t-butyl acrylate (53%), 2-methoxyethyl acrylate (36%), methacrylic acid (11%) Macromonomer side chains: 20% Macromonomer side chains Composition: n-propyl methacrylate (65%); methacrylic acid (35%) Macromonomer side chains MWt: 6,000

(ii) poly(t-butyl acrylate-co-2-methoxyethyl acrylate-co-methacrylic acid)-graft-poly (iso-butyl methacrylate-co-methacrylic acid) MWt of copolymer: 55,000 Backbone: 80% Backbone Composition: t-butyl acrylate (53%), 2-methoxyethyl acrylate (36%), methacrylic acid (11%) Macromonomer side chains: 20% Macromonomer side chains Composition: iso-butyl methacrylate (65%); methacrylic acid (35%) MWt of Macromonomer side chains: 8,000

(iii) poly(t-butyl acrylate-co-2-methoxyethyl acrylate-co-acrylic acid)-graft-[poly (n-propyl methacrylate-co-methacrylic acid); poly(dimethylsiloxane)] MWt of copolymer: 83,000 Backbone: 77% Backbone Composition: t-butyl acrylate (43%), 2-methoxyethyl acrylate (38%), acrylic acid (18%) Macromonomer side chains: 17% Macromonomer side chains Composition: n-propyl methacrylate (60%); methacrylic acid (40%) MWt of Macromonomer side chains: 6,000 Poly (dimethylsiloxane) macromonomer side chains: 6% MWt of poly(dimethylsiloxane): 10,000

(iv) poly(t-butyl acrylate-co-2-methoxyethyl acrylate-co-acrylic acid)-graft-[poly (n-propyl methacrylate-co-methacrylic acid); poly(dimethylsiloxane)] MWt of copolymer:150,000 Backbone: 77% Backbone Composition: t-butyl acrylate (43%), 2-methoxyethyl acrylate (38%), acrylic acid (18%) Macromonomer side chains: 20% Macromonomer side chains Composition: n-propyl methacrylate (60%); methacrylic acid (40%) MWt of Macromonomer side chains: 10,000 Poly (dimethylsiloxane) macromonomer side chains: 3% MWt of poly(dimethylsiloxane): 10,000

The copolymers of the present invention are prepared by the polymerization combination of vinyl monomers and macromonomers. The copolymers can be synthesized by free radical polymerization of the monomers and macromonomers. The general principles of free radical polymerization methods are well understood. See, for example, Odian, "Principles of Polymerization", 3rd edition, John Wiley & Sons, 1991, pp. 198–334, incorporated by reference herein. The desired vinyl monomers and macromonomers are all placed in a reactor, along with a sufficient amount of a mutual solvent so that when the reaction is complete the viscosity of the reaction is reasonable. Undesired terminators, especially oxygen, are removed as needed. This can be done by evacuation or by purging with an inert gas, such as argon or nitrogen. The initiator is introduced and the reaction brought to the temperature needed for initiation to occur, assuming thermal initiators are used. Alternatively, redox or radiation initiation can be used. The polymerization is allowed to proceed as long as needed for a high level of conversion to be achieved, typically from a few hours to a few days. The solvent is then removed, usually by evaporation or by precipitating the copolymer by addition of a nonsolvent. The copolymer can be further purified, as desired.

As an alternative to a batch reaction, the copolymer can be made by a semi-continuous or continuous process. In the semi-continuous process, two or more additions of monomers or macromonomers are made during the polymerization reaction. This is advantageous when the copolymer is made of several monomers which react during the polymerization at different rates. The proportions of monomers added to the reaction at the separate points of addition can be adjusted by one of ordinary skill in the art such that the polymers of the final product have a more uniform structure. In other words, the polymers of the final product will have a more consistent monomer content distribution for each of the monomer types charged to the reaction.

The copolymers are prepared by the polymerization combination of vinyl monomers and macromonomers. The copolymer composition is characterized by the amount of each monomer charged to the polymerization reaction vessel, or alternatively used in a continuous or semi-continuous process.

By appropriate selection and combination of the particular vinyl monomer units and macromonomer units, and by the choice of specific relative ratios of the units well within the ability of one of ordinary skill in the art, the copolymers can be optimized for various physical properties and for compatibility with other ingredients commonly used in hair care applications.

As is be clear to one skilled in the art, the copolymer may have one or more side chains grafted to the backbone. In addition, the compositions of the present invention can include, in addition to the copolymer, low levels of the corresponding copolymers having no side chains grafted to the backbone. As known in the art, synthetic graft copolymerization processes may produce a mixture of polymer molecules containing none, one, or more than one side chains covalently bonded to and pendant from the polymeric backbone. From knowledge of the amount and number average molecular weight of side chains in a polymer sample, and the number average molecular weight of the polymer sample, it is possible to calculate the average number of side chains per polymer backbone.

Personal Care Carrier

The compositions of the present invention comprise from about 0.1% to about 99.9%, preferably from about 0.5% to about 99.0% and most preferably from about 1.0% to about 99.9% of a suitable personal care carrier. Solvents are preferably selected from the group consisting of water, ethanol, n-propanol, isopropanol, and mixtures thereof. The polymers are soluble at a concentration of at least about 0.1 mg/mL, preferably at least about 0.5 mg/mL, and more preferably at least about 1 mg/mL, at about 25° C.

The graft polymers made in accordance with the synthesis methods herein may have acidic functionalities, such as carboxyl groups, and are usually used in at least partially neutralized form to promote solubility/dispensability of the polymer. In addition, use of the neutralized form aids in the ability of the hair styling compositions to be removed from the hair by shampooing. The extent of such neutralization ranges from about 10% to 100%, more preferably from about 20% to about 90%, even more preferably from about 40% to about 85%, neutralization of the acidic functionalities of the graft polymer.

Neutralization of the graft polymers containing acidic functionalities may be accomplished by any conventional or otherwise known technique for effecting such neutralization of by using an organic or inorganic base material. Metallic bases are particularly useful for this purpose. Suitable base neutralizers include, but are not limited to, ammonium hydroxides, alkali metal hydroxides, or an alkaline earth metal hydroxides, preferably potassium hydroxide and sodium hydroxide. Examples of other suitable neutralizing agents include, but are not limited to, amines or amino alcohols such as 2-amino-2-methyl-1,3-propanediol (AMPD), 2-amino-2-ethyl-1,3-ropanediol (AEPD), 2-amino-2-methyl-1-propanol (AMP), 2-amino-1-butanol (AB), monoethanolamine (MEA), diethanolamine (DEA), triethanolamine (TEA), monoisopropanolamine (MIPA), diisopropanolamine (DIPA), triisopropanolamine (TIPA) and dimethyl stearamine (DMS). Preferred are amines and metallic bases.

Neutralization of graft polymers containing basic functionalities, e.g., amino groups, are likewise preferably at least partially neutralized with an organic or inorganic acid e.g., hydrogen chloride. Neutralization can be accomplished by any conventional or otherwise known technique for accomplishing such neutralization. The preferred extent of neutralization is the same as that described for neutralization of acidic functionalities. Solubility for any neutralized graft polymers made in accordance with the method herein should be determined only after the desired acid or base neutralization.

The solvents that are present in hair care compositions are at a level of from about 80% to about 99%, preferably from about 85% to about 98%, more preferably from about 90% to about 95% of the total composition.

The solvents essential to the present compositions are selected from the group consisting of water, $C_2$–$C_3$ monohydric alkanols, and mixtures thereof. If present, $C_3$ alkanols, such as isopropanol, should be used at levels no greater than about 15% by weight of the composition, preferably no greater than about 12%, more preferably no greater than about 10%. High levels of $C_3$ monohydric alcohols are undesirable in the present compositions due to potential odor issues they can create. Preferred polar solvent phases contain water, ethanol, or mixtures thereof.

Where water and alcohol mixtures are used, for instance, water-ethanol or water-isopropanol-ethanol, the water content of the compositions is generally in the range of from about 0.5% to about 99%, preferably from about 5% to about 50% by weight of the total composition. In such mixtures, the alcohol solvents are generally present in the range of from 0.5% to about 99%, preferably from about 50% to about 95%, by weight of the total composition.

In yet another aspect of this invention are provided hair styling products, such as hair spray compositions, which contain reduced levels of volatile organic solvents. A reduced volatile organic solvent hair spray composition of the present invention contains no more than 80% volatile organic solvents (which include, for example, alkanols but not water). As used herein, volatile organic solvents means solvents which have at least one carbon atom and exhibit a vapor pressure of greater than 0.1 mm Hg at 20° C.

In reduced volatile organic solvent hair styling products, the compositions generally comprise at least 10%, by weight, of water. It is also specifically contemplated that they may contain at least about 11%, 12%, 13%, 14%, 15%, or more water.

The reduced volatile organic solvent compositions hereof will comprise up to about 90%, preferably up to about 70%, more preferably up to about 60% even more preferably no more than about 50%, water; and from about 10% to about 80%, preferably from about 20% to about 80%, more preferably from about 40% to about 80%, of volatile organic solvent. It is also contemplated that the compositions can be limited to containing no more than about 75%, 65%, 55%, or other levels of volatile organic solvents.

In addition the compositions could contain branched chain hydrocarbon solvent present at a level of from about 0.1% to about 15%, preferably from about 0.5% to about 10%, more preferably from about 2% to about 8%, by weight of the composition. Also useful are low boiling point silicone oils.

The branched chain hydrocarbon solvent is characterized by a boiling point of at least about 105° C., preferably at least about 110° C., more preferably at least about 125° C., most preferably at least about 150° C. The boiling point is also generally about 260° C. or less, preferably about 200° C. or less. The hydrocarbon chosen should also be safe for topical application to the hair and skin.

The branched chain hydrocarbon solvents are selected from the group consisting of $C_{10}$–$C_{14}$ branched chain hydrocarbons, and mixtures thereof, preferably $C_{11}$–$C_{13}$ branched chain hydrocarbons, more preferably $C_{12}$ branched chain hydrocarbons. Saturated hydrocarbons are preferred, although it isn't necessarily intended to exclude unsaturated hydrocarbons.

Examples of suitable nonpolar solvents include isoparaffins of the above chain sizes. Isoparaffins are commercially available from Exxon Chemical Co. Examples include Isopar™ G ($C_{10}$–$C_{11}$ isoparaffins), Isopar™ H and K ($C_{11}$–$C_{12}$ isoparaffins), and Isopar™ L ($C_{11}$–$C_{13}$ isoparaffins). The most preferred nonpolar solvent are $C_{12}$ branched chain hydrocarbons, especially isododecane. Isododecane is commercially available from Preperse, Inc. (South Plainfield, N.J., U.S.A.) as Permethyl™ 99A.

Plasticizer

The compositions hereof can optionally contain a plasticizer for the grafted polymer. Any plasticizer suitable for use in hair care products or for topical application to the hair or skin can be used. A wide variety of plasticizers are known in the art. These include acetyl triethylcitrate, triethycitrate, glycerin, diisobutyl adipate, butyl stearate, and propylene glycol. Plasticizers are typically used at levels of from about 0.01% to about 10%, by weight of the composition, preferably from about 0.05% to about 3%, more preferably from about 0.05% to about 1%.

Optional Components

Adhesive Polymer

The compositions of the present invention can comprise an additional adhesive polymer. The compositions hereof will generally comprise from about 0.1% to about 15%, preferably from 0.5% to about 8%, more preferably from about 1% to about 8%, by weight of the composition, of the adhesive polymer. It is not intended to exclude the use of higher or lower levels of the polymers, as long as an effective amount is used to provide adhesive or film-forming properties to the composition and the composition can be formulated and effectively applied for its intended purpose. By adhesive polymer what is meant is that when applied as a solution to a surface and, dried, the polymer forms a film. Such a film will have adhesive and cohesive strength as is understood by those skilled in the art.

The polymeric backbone is chosen such that it is compatible with the adhesive styling polymer. By "compatible" is meant is that, when placed in a suitable solvent, the polymers form a stable solution, i.e., the polymers do not compete for solubility and therefore, cause no phase separation and when the solution is dried a uniform film is formed, with no macrophase separation of the two polymers. A suitable solvent is a solvent which substantially completely dissolves the non-silicone and silicone grafted polymers at the levels described herein. The polymer blend forms a relatively clear hairspray system (% transmittance at 450 nm is generally greater than 80%). It is recognized that certain plasticizers can form cloudy films as well as incorrect neutralization levels. Therefore, this would fall outside this definition of compatibility. The compatibility can be tested by dissolving the polymers in a mutual solvent, and then evaporating the solvent to form a film. Incompatible polymers will form a cloudy film with poor mechanical properties, due to the large scale phase separation of the two polymers. Although compatibility can occur between two polymers of completely different structures, it is preferred that compatibility be obtained by making the composition of the respective backbones similar to or identical to one another.

The adhesive polymer should have a weight average molecular weight of at least about 20,000, preferably greater than about 25,000, more preferably greater than about 30,000, most preferably greater than about 35,000. There is no upper limit for molecular weight except that which limits applicability of the invention for practical reasons, such as processing, aesthetic characteristics, formulateability, etc. In general, the weight average molecular weight will be less than about 10,000,000, more generally less than about 5,000,000, and typically less than about 2,000,000. Preferably, the weight average molecular weight will be between about 20,000 and about 2,000,000, more preferably between about 30,000 and about 1,000,000, and most preferably between about 40,000 and about 500,000.

Preferably the weight ratio of the toughened graft polymer of the present invention to adhesive polymer ranges from about 1:10 to about 1:1, preferably from about 1:5 to about 1:1.

Exemplary adhesive polymers for use in the present invention include the following, where the numbers following the structure indicate the weight ratios of monomers as loaded into the polymerization reactor:

(i) acrylic acid/t-butyl acrylate 25/75

(ii) dimethylaminoethyl methacrylate/isobutyl methacrylate/2-ethylhexyl-methacrylate 40/40/20

(iii) t-butylacrylate/acrylic acid 65/35

(iv) polymer (ii) quaternized by treatment with methyl chloride

The adhesive polymers can be synthesized as described above such as by free radical polymerization of the monomers.

Solubility of the adhesive polymer, as described above, should be determined after neutralization, if any, as well as after addition of other ingredients that may be included in the polar solvent phase, such as surfactants, solubilizers, etc.

The present compositions can contain a wide variety of additional optional ingredients, including among them any of the types of ingredients known in the art for use in hair setting compositions, especially hair spray compositions and hair setting tonics. These ingredients include, but are not limited to, surfactants (including fluorinated surfactants and silicone copolyols), and ionic strength modifiers, propellants, hair conditioning agents (e.g., silicone fluids, fatty esters, fatty alcohols, long chain hydrocarbons, cationic surfactants, etc.)

Ionic Strength Modifier System

Optionally, the compositions of the present invention can contain an effective amount of a non-surface active ionic strength modifier system for reducing the viscosity of the hair spray composition. When used, the ionic strength modifiers will be present in the present compositions at a level of at least about 0.01%, by weight of the composition. The upper limit is dependent upon the maximum amount of the ionic strength modifiers that can be present in the particular compositions hereof such that the hair setting resin remains solubilized or dispersed. As will be understood by those skilled in the art, as the ionic strength of the composition is increased, the resin will eventually fall out of solution, or otherwise no longer remain solubilized or dispersed in the polar liquid carrier. The upper limit of the ionic strength modifier system level will vary depending upon the particular ionic strength modifiers, liquid vehicle, resin, and other ingredients present in the composition. Thus, for example, the maximum amount of the ionic strength modifiers that can be used will tend to be lower for compositions with liquid vehicles containing less water, compared to compositions with more water. Generally, the compositions will comprise about 4%, by weight, or less of the ionic strength modifiers, more generally about 2% or less, and typically about 1% or less. Preferably, the compositions hereof will comprise from about 0.01% to about 0.5%, more preferably from about 0.01% to about 0.1%, of the ionic strength modifier system.

The ionic strength modifier system comprises a mixture of monomeric cations and anions. The ions of the ionic strength modifier system hereof are non-surface active, i.e. they do not significantly reduce surface tension. For purposes hereof, non-surface active shall mean the ions, which at a 0.5% aqueous solution concentration, reduce surface tension by no more than 5.0 dynes/cm2. Generally, the ions of the ionic strength modifier system hereof will be characterized by having, at maximum, four or less carbon atoms per charge, preferably two or less carbon atoms, in any aliphatic chain or straight or branched chain organic heterochain.

The ionic strength modifier system comprises monomeric ions of the type which are products of acid-base reactions. Thus, basic and acidic ions $OH^-$ and $H^+$ do not constitute part of the ionic strength modifier system hereof, although they may be present in the composition. The ions hereof are incorporated into the composition in a form such that they can exist in the composition as free ions, i.e., in dissociated form. It is not necessary that all of the ions added exist in the composition as free ions, but must be at least partially soluble or dissociated in the composition. The ionic strength modifiers can be incorporated into the hair styling compositions, for example, by addition of soluble salts, or by addition of mixtures of acids and bases, or by a combination thereof. It is a necessary aspect of the invention that both anions and cations of the ionic strength modifier system be included in the composition.

Suitable cations for use include, for example, alkali metals, such as lithium, sodium, and potassium, and alkaline-earth metals, such as magnesium, calcium, and strontium. Preferred of the divalent cations is magnesium. Preferred monovalent metal ions are lithium, sodium, and potassium, particularly sodium and potassium. Suitable means of addition to the compositions hereof include, for example, addition as bases, e.g., hydroxides, sodium hydroxide and potassium hydroxide, and such as salts that are soluble in the liquid carrier, e.g. salts of monomeric anions such as those described below.

Other suitable cations include organic ions, such as quaternary ammonium ions and cationic amines, such as ammonium mono-, di-, and tri-ethanolamines, triethylamine, morpholine, aminomethylpropanol (AMP), aminoethylpropanediol, etc. Ammonium and the amines are preferably provided in the forms of salts, such as hydrochloride salts.

Monomeric anions that can be used include halogen ions, such as chloride, fluoride, bromide, and iodide, particularly chloride, sulfate, ethyl sulfate, methyl sulfate, cyclohexyl sulfamate, thiosulfate, toluene sulfonate, xylene sulfonate, citrate, nitrate, bicarbonate, adipate, succinate, saccharinate, benzoate, lactate, borate, isethionate, tartrate, and other monomeric anions that can exist in dissociated form in the hair styling composition. The anions can be added to the compositions hereof, for example, in the form of acids or salts which are at least partially soluble in the liquid vehicle, e.g., sodium or potassium salts of acetate, citrate, nitrate, chloride, sulfate, etc. Preferably, such salts are entirely soluble in the vehicle.

The use of ionic strength modifiers are especially useful in reduced volatile organic solvent compositions, most especially those utilizing silicone macromer-containing polymers.

Personal Care Compositions

The present invention encompasses a wide variety of personal care compositions, including shampoos, soaps, lotions, creams, antiperspirants, nail enamels, lipsticks, foundations, mascaras, sunscreens, hair spray compositions, mousses, and hair setting tonics. Compositions that will be flowable, e.g., low viscosity compositions that, preferably, are suitable for spray application as well as higher viscosity compositions are also contemplated.

Personal care carriers are suitable for use in the present invention are described in U.S. Pat. No. 5,306,485 to Robinson et al., issued Apr. 26, 1994, and U.S. Pat. No. 5,002,680 to Schmidt et al., issued Mar. 26, 1991, both of which are incorporated by reference herein. Hair spray compositions and mousses of the present invention can be dispensed from containers which are aerosol dispensers or pump spray dispensers. Such dispensers, i.e., containers, are well known to those skilled in the art and are commercially available from a variety of manufacturers, including American National Can Corp. and Continental Can Corp.

When the hair spray compositions are to be dispensed from a pressurized aerosol container, a propellant which consists of one or more of the conventionally-known aerosol propellants may be used to propel the compositions. A suitable propellant for use can be generally any liquifiable gas conventionally used for aerosol containers.

Suitable propellants for use are volatile hydrocarbon propellants which can include liquefied lower hydrocarbons of 3 to 4 carbon atoms such as propane, butane and isobutane. Other suitable propellants are hydrofluorocarbons such as 1,2-difluoroethane (Hydrofluorocarbon 152A) supplied as Dymel 152A by DuPont. Other examples of propellants are dimethylether, N-butane, isobutane, propanes, nitrogen, carbon dioxide, nitrous oxide and atmospheric gas and mixtures thereof.

The aerosol propellant may be mixed with the present compositions and the amount of propellant to be mixed is governed by normal factors well known in the aerosol art. Generally, for liquifiable propellants, the level of propellant is from about 10% to about 60% by weight of the total composition, preferably from about 15% to about 40% by weight of the total composition.

Alternatively, pressurized aerosol dispensers can be used where the propellant is separated from contact with the hair spray composition such as a two compartment can of the type sold under the tradename SEPRO from American National Can Corp.

Other suitable aerosol dispensers are those characterized by the propellant being compressed air which can be filled into the dispenser by means of a pump or equivalent device prior to use. Such dispensers are described in U.S. Pat. No. 4,077,441, Mar. 7, 1978, Olofsson and U.S. Pat. No. 4,850,577, Jul. 25, 1989, TerStege, both incorporated by reference herein, and in U.S. Ser. No. 07/839,648, Gosselin et al., filed Feb. 21, 1992, also incorporated by reference herein. Compressed air aerosol containers suitable for use are also currently marketed by The Procter & Gamble Company under their tradename VIDAL SASSOON AIRSPRAY® hair sprays.

Conventional non-aerosol pump spray dispensers, i.e., atomizers, can also be used.

Other hair styling compositions include tonics and lotions, which are typically dispensed in a conventional bottle or tube, and applied directly to the hair or first dispensed to the hand and then to the hair.

The hair styling formulations of the present invention can optionally contain conventional hair care composition adjuvants. Generally, adjuvants collectively can comprise from about 0.05% to about 5% by weight and preferably from about 0.1% to about 3%, by weight. Such conventional optional adjuvants are well known to those skilled in the art and include in addition to those discussed above, emollients; lubricants and penetrants such as various lanolin compounds; protein hydrolysates and other protein derivatives; ethylene adducts and polyoxyethylene cholesterol; dyes, tints, bleaches, reducing agents and other colorants; pH adjusting agents sunscreens; preservatives; thickening agents (e.g. polymeric thickeners, such as xanthan gum); and perfume.

Method Of Marking

The personal care compositions of the present invention can be made using conventional formulation and mixing techniques.

Method Of Use

The compositions of the present invention are used in conventional ways to provide the personal care compositions of the present invention. Such method generally involves application of an effective amount of the product. For example, in a hair spray composition, said composition is applied to the desired dry, slightly damp, or wet hair before and/or after the hair is arranged to a desired style. The composition is then dried or allowed to dry. By "effective amount" is meant an amount sufficient to provide the desired benefits.

The following Experimentals and Examples further illustrate embodiments within the scope of the present invention. They are given solely for the purposes of illustration and are not to be construed as limitations of the present invention as many variations of the invention are possible without departing from its spirit and scope.

EXPERIMENTALS

The following synthesis exemplify grafted polymers useful in the present compositions.

Synthesis of para-vinyl benzoyl chloride

To a clean round bottom flask with an argon atmosphere and equipped with magnetic stir bar is added para-vinyl benzoic acid (10 g, 0.067 mole) which is suspended in benzene (25 ml). Oxalyl chloride (25 g, 0.197 mole) is added to the flask. The mixture is stirred for 8 hours and continuously flushed with a continuous stream of argon to purge the system of the gases generated during the reaction. Solvent and excess oxalyl chloride is stripped off under vacuum. Finally, the product is distilled under vacuum to yield para-vinyl benzoyl chloride. Approximately 90% of the theoretical yield is obtained.

Synthesis of Vinylphenyl-terminated Poly(n-propyl methacrylate-co-methacrylic acid) Macromonomer Into a round-bottomed-flask fitted with magnetic stirring and under slight argon pressure (8 psi), is added tetrahydrofuran (1 L), trimethylsilylmethacrylate (100 g, 0.632 mole), and n-propylmethacrylate (100 g, 0.780 mole). The solution is cooled to −78° C. then initiated with diphenylhexyllithium (0.0275 moles) (prepared by adding 1:1 mole ratio of sec-butyl lithium and 1,1-diphenyl ethylene in THF) for chain propagation via anionic polymerization mechanism. After continuous stirring for 0.5 h, vinylbenzoyl chloride (8.33 mL, 0.05 mole) is charged to the solution and continued stirring for 0.5 h. The solution is then warmed to ambient temperature and H₂O (10 mL) is added and stirred for 0.25 hours to deprotect the acid groups. The macromonomer, which has a weight average molecular weight of about 6000, is obtained by precipitating the resulting solution in hexanes, collecting precipitate, and drying under vacuum.

Copolymer 1

Synthesis of Poly(t-butylacrylate-co-2-methoxyethylacrylate-co-acrylic acid)-graft-[poly(n-propyl methacrylate-co-Methacrylic Acid):Poly(dimethylsiloxane)] Copolymer To a round-bottomed-flask equipped with a reflux condenser, temperature control, mechanical stirring mechanism, and under slight argon pressure (8 psi), is added acetone (0.5 L), t-butylacrylate (22.3 g), 2-methoxyethylacrylate (36 g), acrylic acid (18 g), poly (dimethylsiloxane) macromonomer (6 g) (Chisso Corp. Tokyo, Japan), and vinylphenyl-terminated (n-propylmethacrylate-co-methacrylic acid) macromonomer (18 g) (from Example 2). Solution is stirred until all components are dissolved, then heated to 60° C. Azobisisobutyronitrile (0.7 g) is charged to the system. After 10 h, solution is cooled and precipitated in water to yield silicone modified graft copolymer.

Copolymer 2

Synthesis of Poly(t-butylacrylate-co-2-methoxyethylacrylate-co-methacrylic acid)-graft-[poly(n-propyl methacrylate-co-methacrylic Acid) Copolymer To a round-bottomed-flask equipped with a reflux condenser, temperature control, mechanical stirring mechanism, and under slight argon pressure (8 psi), is added acetone (0.5 L), t-butylacrylate (42.4 g), 2-methoxyethyl acrylate (29 g), methacrylic acid (9 g), and vinylphenyl-terminated (n-propylmethacrylate-co-methacrylic acid) macromonomer (20 g) (from Example 2). Solution is stirred until all components are dissolved, then heated to 60° C. Azobisisobutyronitrile (0.5 g) is charged to the system. After 1 h, solution is cooled and precipitated in water to yield the graft copolymer.

EXAMPLES

Examples 1–4

The following examples represent nonaerosol hairspray compositions of the present invention.

|  | Example No | | | |
| --- | --- | --- | --- | --- |
| Component (wt. %) | 1 | 2 | 3 | 4 |
| Copolymer[1] | 4.00 | 4.75 | 5.50 | 5.50 |
| Isododecane[2] | 1.00 | 1.00 | 1.00 | 3.00 |
| Diisopropyl butyl adipate | 0.40 | 0.75 | 0.90 | 0.55 |
| Sodium hydroxide[3] | 0.96 | 1.20 | 1.44 | 1.6 |
| Perfume | 0.10 | 0.10 | 0.10 | 0.10 |
| Water | 17.00 | 20.00 | 20.00 | 18.00 |
| Ethanol[4] | 76.54 | 71.95 | 70.56 | 71.25 |

[1]Copolymer 1
[2]PERMETHYL 99A, from Presperse, Inc., South Plainfield, NJ, USA.
[3]Sodium hydroxide is 30% active.
[4]SDA 40 (100% ethanol).

Example 5

The following is a hair conditioner composition representative of the present invention.

| Ingredients | Weight % |
| --- | --- |
| Water | Q.S. to 100% |
| Perfume | 0.10 |
| Stearalkonium Chloride | 0.87 |
| Methylchloroisothiazolinone Methylisothiazolinone | 0.03 |
| Sodium Hydroxide Solution (30% by weight) | 0.70 |
| Copolymer 1 | 3.00 |
| Ethanol | 20.0 |

This product is prepared by dispersing the Copolymer 1 in ethanol then adding the remaining ingredients and stirring for about 30 minutes.

Example 6

The following is a hair styling gel composition representative of the present invention.

| Ingredients | Weight % |
| --- | --- |
| Copolymer 2 | 2.50 |
| Water | QS 100% |
| Carbomer 940 | 0.50 |
| Sodium Hydroxide Solution (30% by weight) | 0.80 |
| Panthenol | 0.05 |
| Polysorbate 80 | 0.20 |
| Perfume | 0.20 |

This product is prepared by dispersing the Copolymer 2 and carbomer 940 in water and adding the sodium hydroxide. The mixture is stirred for approximately one half hour and the remaining components are added.

Example 7

The following is a spray-on gel hair composition representative of the present invention.

| Ingredients | Weight % |
| --- | --- |
| Water | Q.S. to 100% |
| Ethanol | 15.00 |
| Panthenol | 0.05 |
| Potassium Hydroxide Solution (45% by weight) | 0.50 |
| Perfume | 0.20 |
| Copolymer 1 | 2.00 |

This product is prepared by dissolving the Copolymer 1 in ethanol and then adding the water and potassium hydroxide solution to facilitate the incorporation of the copolymer into the solvent. The mixture is stirred for one half hour and the other components are mixed in.

Example 8

The following is a hair styling mousse composition representative of the present invention.

| Ingredients | Weight % |
| --- | --- |
| Water | Q.S. to 100% |
| Lauramine Oxide | 0.20 |

-continued

| Ingredients | Weight % |
| --- | --- |
| Panthenol | 0.05 |
| Perfume | 0.05 |
| Copolymer 2 | 3.00 |
| Sodium Hydroxide Solution (30% by weight) | 1.00 |
| Isobutane | 7.00 |

This product is prepared by dissolving the Copolymer 2 in water and adding the sodium hydroxide solution with mixing for one half hour. The other components (except isobutane) are added and mixed for an additional 10 minutes. Aluminum aerosol cans are then filled with 93 parts of this batch, affixed with a valve which is crimped into position, and lastly pressure filled with 7 parts Isobutane. This composition is useful for application to the hair to provide conditioning, styling and hold.

Example 9

| Sunscreen Composition | |
| --- | --- |
| Ingredients | Weight % |
| Water | QS100 |
| Carbomer 1342[1] | 0.16 |
| Octyl Methoxycinnamate | 0.50 |
| Dimethicone copolyol | 0.10 |
| Tocopheryl Acetate | 0.10 |
| Sodium Hydroxide (30% sol. by weight) | 1.50 |
| Ethanol | 40.00 |
| Copolymer 2 | 4.00 |

[1]Available as Carbopol ® 1342 from B. F. Goodrich.

The water, ethanol, sodium hydroxide solution and Copolymer 2 are mixed for one half hour. The remaining ingredients are added and mixed for an additional half hour.

Example 10

The following is an anti-acne composition representative of the present invention.

| Ingredients | Weight % |
| --- | --- |
| Copolymer 1 | 2.00 |
| Water | Q.S. to 100% |
| Ethanol (SDA 40) | 40.00 |
| Carbomer 940 | 0.75 |
| Sodium Hydroxide Solution (30% by weight) | 0.90 |
| Salicylic Acid | 2.00 |

This product is prepared by mixing the water, ethanol, Copolymer 1, and carbomer together for about 10 minutes. The remaining ingredients are added and the mixture is stirred for an additional 30 minutes. This composition is useful for application to the skin to provide improved water resistance and is useful in the treatment of acne.

Example 11

The following is a nail polish clear coat composition representative of the present invention.

| Ingredients | Weight % |
| --- | --- |
| Copolymer 2 | 15.00 |
| Ethanol | 42.00 |
| Acetone | 40.00 |
| NaOH soln., 30% | 3.00 |

This product is prepared by mixing all the ingredients until dispersed.

Example 12

The following is a facial wrinkle remover composition representative of the present invention.

| Ingredients | Weight % |
| --- | --- |
| Copolymer 2 | 6.00 |
| NaOH soln., 30% | 2.10 |
| DRO water | q.s. |

This product is prepared by mixing all the ingredients until dispersed.

Example 13

The following is a styling lotion composition representative of the present invention.

| Ingredients | Weight % |
| --- | --- |
| Copolymer 1 | 4.00 |
| Natrosol 250HH[1] | 0.50 |
| NaOH soln., 30% | 1.35 |
| Kathon CG | 0.03 |
| Ethanol | 8.00 |
| DRO water | q.s. |

Example 14

The following is an aftershave splash composition representative of the present invention.

| Ingredients | Weight % |
| --- | --- |
| Copolymer 1 | 2.00 |
| NaOH soln., 30% | 0.60 |
| Ethanol | 50.00 |
| Perfume | 0.20 |
| Menthol | 0.20 |
| DRO water | q.s. |

This product is prepared by mixing all the ingredients until dispersed.

What is claimed is:
1. A composition comprising:
(a) an adhesive copolymer, said copolymer being characterized by an organic polymeric backbone wherein said backbone has a $T_g$ of from about 0° C. to about 45° C. wherein said copolymer comprises one or more side chains grafted thereon consisting of acrylic and methacrylic monomer units wherein said side chains have a $T_g$ of from about 50° C. to about 200° C. wherein the number average molecular weight of said side chain is greater than about 1000; and (b) a personal care carrier comprising a solvent selected from the group consisting of water, $C_2$–$C_3$ monohydric alkanols and mixtures thereof, wherein the composition is a personal care composition.

2. A composition according to claim 1, wherein said backbone monomer unit is selected from the group consisting of unsaturated alcohols, unsaturated monocarboxylic acids, unsaturated dicarboxylic acids, unsaturated anhydrides, alcohol esters of unsaturated monocarboxylic acids, alcohol esters of unsaturated dicarboxylic acids, alcohol esters of unsaturated anhydrides, alkoxylated esters of unsaturated monocarboxylic acids, alkoxylated esters of unsaturated dicarboxylic acids, alkoxylated esters of unsaturated anhydrides, aminoalkyl esters of unsaturated monocarboxylic acids, aminoalkyl esters of unsaturated dicarboxylic acids, aminoalkyl esters of unsaturated anhydrides, amides of unsaturated monocarboxylic acids, amides of unsaturated dicarboxylic acids, amides of unsaturated anhydrides, salts of unsaturated monocarboxylic acids, salts of unsaturated dicarboxylic acids, salts of unsaturated anhydrides, unsaturated hydrocarbons, unsaturated heterocycles, and mixtures thereof.

3. A composition according to claim 2, wherein said backbone monomer unit is selected from the group consisting of acrylic acid, methacrylic acid, N,N-dimethyl acrylamide, dimethylaminoethyl methacrylate, quaternized dimethylaminoethyl methacrylate, vinyl pyrrolidone, $C_1$–$C_{18}$ alkyl esters of acrylic or methacrylic acid, styrene, alpha-methylstyrene, t-butylstyrene, vinyl acetate, vinyl propionate, vinyl chloride, vinylidene chloride, vinyl toluene, 2-methoxyethyl acrylate, n-butyl methacrylate, isobutyl methacrylate, t-butyl acrylate, t-butyl methacrylate, 2-ethylhexyl methacrylate, methyl methacrylate, salts of any acids and amines listed above, and combinations thereof.

4. A composition according to claim 3, wherein said backbone monomer unit is selected from the group consisting of acrylic acid, methacrylic acid, 2-methoxyethyl acrylate, n-butyl methacrylate, isobutyl methacrylate, t-butyl acrylate, t-butyl methacrylate, 2-ethylhexyl methacrylate, methyl methacrylate and mixtures thereof.

5. A composition according to claim 4, wherein the backbone of has a Tg of from about 0° C. to about 45° C.

6. A composition according to claim 5, wherein the said backbone of (i) has a Tg of from about 0° C. to about 35° C.

7. A composition according to claim 6 wherein the said backbone of (i) has a Tg of from about 0° C. to about 25° C.

8. A composition according to claim 1, wherein said side chain has general formula:

$$[I]_n\text{-}[W]_m\text{-}E$$

wherein I is an initiator, n=0 or 1, W is a monomer unit from the group consisting of acrylic monomer units, methacrylic monomer units and mixtures thereof, E is an endcapping group, and m is an integer from about 10 to about 2000.

9. A composition according to claim 8, wherein said monomer unit of said side chain is selected from the group consisting of an acrylic acid monomer unit, a methacrylic acid monomer unit and mixtures thereof. Nonlimiting classes of such monomers include $C_1$–$C_{18}$ straight and branched chain acrylate esters and $C_1$–$C_{18}$ straight and branched chain methacrylate esters, and mixtures thereof.

10. A composition according to claim 9, wherein said monomer unit of each of said side chains is selected from the monomer units are selected from the group consisting acrylic acid, methacrylic acid, n-propyl methacrylate, iso-butyl methacrylate, tert-butyl acrylate, tert-butyl methacrylate, 2-hydroxyethyl methacrylate, 2-hydroxypropyl methacrylate.

11. A composition according to claim 10, wherein said monomer units of each of said side chains is selected from the group consisting of acrylic acid, methacrylic acid, n-propyl methacrylate, iso-butyl methacrylate and mixtures thereof.

12. A composition according to claim 11, wherein each side chain of said polymer has a Tg of from about 50° C. to about 200° C.

13. A composition according to claim 12, wherein each side chains of said polymer has a Tg of from about 60° C. to about 150° C.

14. A composition according to claim 13, wherein each side chains of said polymer has a Tg of from about 70° C. to about 110° C.

15. A composition according to claim 1, wherein said backbone further comprises one or more side chains having a polysiloxane-containing macromonomer units, wherein said polysiloxane-containing macromonomer side chains have a weight average molecular weight from about 1,000 to about 50,000, and correspond to the chemical formula:

$$X(Y)_n Si(R)_{3-m}(Z)_m$$

wherein:

X is a vinyl group copolymerizable with said vinyl monomer units;

Y is a divalent linking group;

R is selected from the group consisting of hydrogen, hydroxyl, C1–C6 alkyl, C1–C6 alkoxy, C2–C6 alkylamino, phenyl, C1–C6 alky or alkoxy-substituted phenyl;

Z is a monovalent siloxane polymeric moiety having a number average molecular weight of at least about 1000, is essentially unreactive under copolymerization conditions, and is pendant from said vinyl polymeric backbone after polymerization;

n is 0 or 1;and m is an integer from 1 to 3.

16. A composition according to claim 15 wherein said polysiloxane-containing macromonomer units are selected from the group consisting of

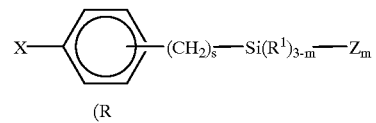

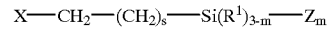

and

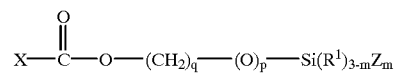

wherein s is 0, 1, 2, 3, 4, 5 or 6; m is 1, 2 or 3; p is 0; q is 2, 3, 4, 5 or 6; $R^1$ is selected from the group consisting of hydrogen, hydroxyl, C1–C6 alkyl, C1–C6 alkoxy, C2–C6 alkylamino, phenyl, C1–C6 alkyl or alkoxy-substituted phenyl, $R^2$ is selected from the group consisting of C1–C6 alkyl or C1–C6 alkyl substituted phenyl; n is 0, 1, 2, 3 or 4; X is

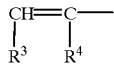

wherein $R^3$ is hydrogen or —COOH; $R^4$ is hydrogen, methyl or —CH$_2$COOH; Z is

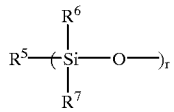

$R^5$, $R^6$, and $R^7$ independently selected from the group consisting of hydrogen, hydroxyl, C1–C6 alkyl, C1–C6 alkoxy, C2–C6 alkylamino, phenyl, C1–C6 alkyl or alkoxy-substituted phenyl, and r is an integer of from about 14 to about 700.

17. A composition according to claim 16 wherein said polysiloxane-containing macromonomer units correspond to the chemical formula:

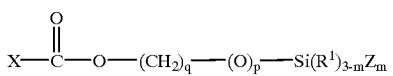

wherein m is 1; p is 0; q is 3; $R^1$ is methyl; X is

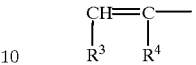

wherein $R^3$ is hydrogen; $R^4$ is methyl; and Z is

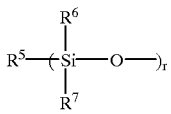

$R^5$, $R^6$, and $R^7$ are independently selected from the group consisting of hydrogen, hydroxyl, C1–C6 alkyl, C1–C6 alkoxy, C2–C6 alkylamino, phenyl, C1–C6 alkyl or alkoxy-substituted phenyl, and r is an integer of from about 14 to about 700.

18. A composition according to claim 1 wherein the composition is in the form of a shampoo, soap, lotion, cream, antiperspirant, nail enamel, lipstick, foundation, mascara, sunscreen, hair spray, mousse or hair setting tonic.

* * * * *